United States Patent [19]

Semrow et al.

[11] Patent Number: 4,510,941

[45] Date of Patent: Apr. 16, 1985

[54] TEMPERATURE, PULSE AND RESPIRATION MOUTHPIECE PROBE

[75] Inventors: Carolyn M. Semrow, Island Lake; Mark W. Kolstedt, Cary; William J. Dunn, Libertyville, all of Ill.

[73] Assignee: The Kendall Company, Walpole, Mass.

[21] Appl. No.: 412,535

[22] Filed: Aug. 30, 1982

[51] Int. Cl.³ ............................................. A61B 5/00
[52] U.S. Cl. .................................... 128/671; 128/687; 128/736
[58] Field of Search ................................. 128/670–671, 128/736, 687–690, 721, 724

[56] References Cited

U.S. PATENT DOCUMENTS

| 358,141 | 2/1887 | Barry | 128/736 |
|---|---|---|---|
| 2,445,539 | 7/1948 | Singer | 128/736 |
| 2,797,682 | 7/1957 | Kannenberg | 128/736 |
| 2,817,236 | 12/1957 | Van Alstyne, Jr. | 128/736 |
| 3,733,905 | 5/1973 | Bremer | 128/736 |
| 3,780,586 | 12/1973 | Donofrio | 128/736 |
| 4,036,211 | 7/1977 | Veth et al. | 128/736 X |
| 4,053,951 | 11/1977 | Hudspeth et al. | 128/736 X |
| 4,090,504 | 5/1978 | Nathan | 128/736 X |
| 4,121,574 | 10/1978 | Lester | 128/736 X |

OTHER PUBLICATIONS

Berne & Levy "Cardiovascular Physiology", C. V. Mosby Co., St. Louis 1972, p. 135.

Primary Examiner—Lee S. Cohen
Assistant Examiner—Francis J. Jaworski
Attorney, Agent, or Firm—James W. Potthast

[57] ABSTRACT

A temperature, pulse and respiration probe having a mouthpiece which fits over the patient's teeth and carries a thermistor for sensing the patient's temperature and a reflective photodetector for sensing both the patient's pulse and the patient's respiration. The reflective photodetector is mounted adjacent to a part of the interior surface of the patient's mouth which relatively rapidly, periodically changes its reflectivity due to the patient's pulse and which also relatively slowly, periodically changes its reflectivity due to the patient's respiration. The photodetector produces a single signal representative of both the relatively rapid and the relatively slower changes in the reflectivity corresponding to the patient's pulse and respiration rate, respectively. In one embodiment, all of these sensors are mounted to a portion of the mouthpiece adjacent the patient's inner gum. In another embodiment the sensors are mounted to a portion of the mouthpiece which underlies the patient's tongue. The patient's frenulum linguae is received within a notch in the underlying portion and the thermistor and photodetector are mounted at opposite sides of the notch.

48 Claims, 6 Drawing Figures

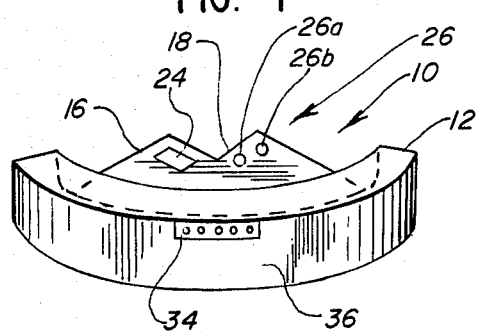
FIG. 1
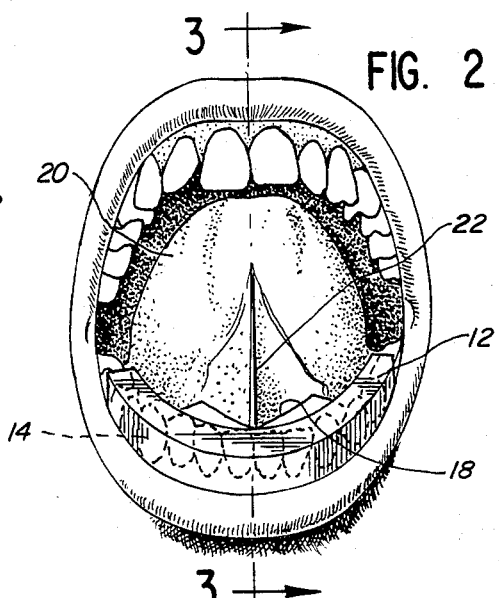
FIG. 2
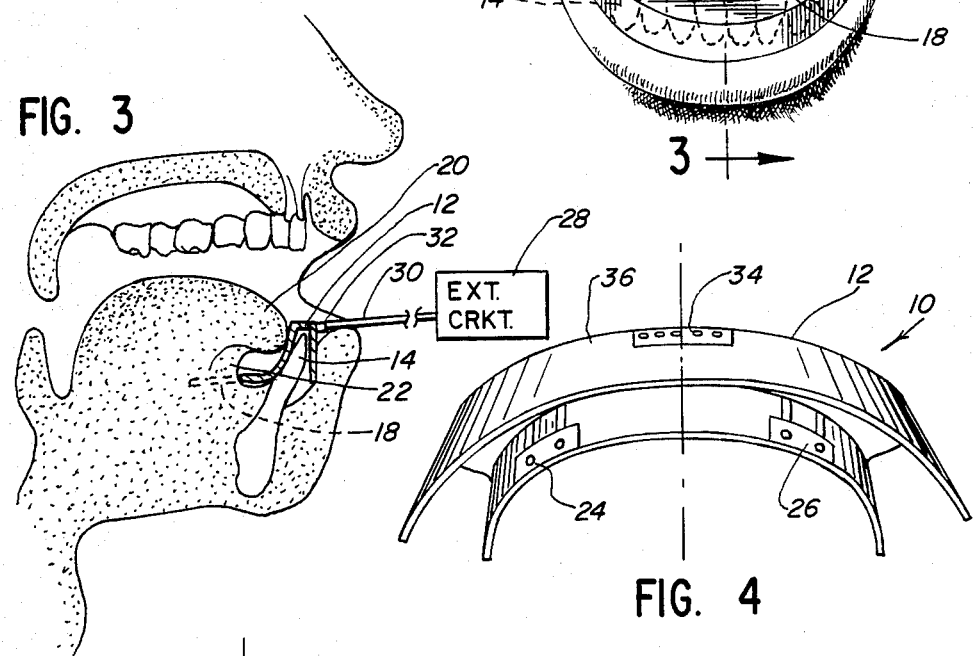
FIG. 3
FIG. 4
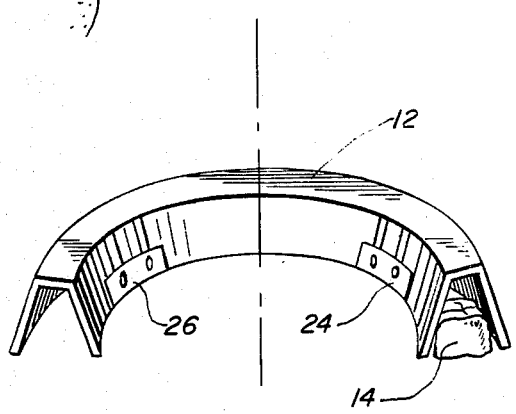
FIG. 5
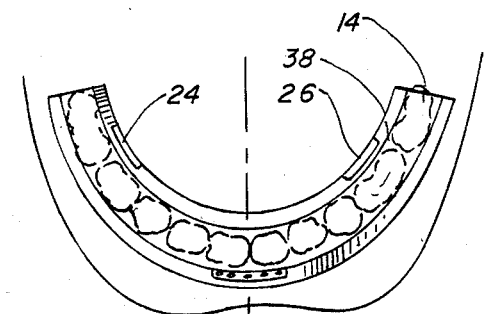
FIG. 6

TEMPERATURE, PULSE AND RESPIRATION MOUTHPIECE PROBE

BACKGROUND OF THE INVENTION

This invention relates to probes for sensing one or more of a patient's temperature, pulse rate and respiration rate and, more particularly, to such a probe in which the sensing means of the probe are electronic.

It is necessary in providing health care to patients to quickly and accurately determine the patient's temperature, pulse rate and respiration rate. Often, it is desirable to concurrently obtain the values of all three of these vital signs. Traditional methods, such as require the use of mercury thermometers for temperature measurement or the use of watches for respiration or pulse rate, are often less than completely accurate and are too difficult in their execution to permit easy concurrent measurement or rapid measurement.

Accordingly, in recent times, techniques have been developed for measuring these vital signs by electronic means, and probes have been developed which employ these electronic means to concurrently measure a plurality of the vital signs through use of a single probe. An example of such a multifunction probe is shown in U.S. Pat. No. 4,202,353 of Hirsch et al. in which both the patient's temperature and respiration are sensed by thermistors. One thermistor is located beneath the patient's tongue to sense body temperature, and the other thermistor is located in the path of the patient's nasal passageway to sense respiration rate. These sensors are mounted to a mouthpiece which, in turn, is covered by a sheath.

Other mouthpieces for making like measurements are known, and examples may be found in U.S. Pat. Nos. 3,410,264 of Frederik and 3,940,251 of Jones et al. In the Frederik patent, the mouthpiece is used as part of an instrument for measuring total respiratory and nasal air resistance. In the Jones et al. patent, a person exhales through a detachable mouthpiece which provides an electrical output dependent upon the amount of alcohol in the breath sample.

Other sensing means have also been utilized to make measurements of this type. For instance, in U.S. Pat. No. 3,736,918 of Mutschelknauss et al. blood flow in the mucous membranes or the gum of a patient is measured by electronically magnifying the area being investigated to visually ascertain the blood flow velocity. The use of photoplethysmographs for making various blood pressure measurements or the like is also well known.

These probes and the variety of sensing means used in association therewith lack means for insuring that the sensors are properly located within a patient's mouth so that the sensors will accurately sense true temperature or whatever other function is being sensed. In addition, the advantages of fast and accurate measurement obtained from the use of reflective photodetectors for the sensing of pulse or respiration rate have not been realized in such mouthpiece probes.

SUMMARY OF THE INVENTION

One of the important objects of the present invention is to provide a probe with a mouthpiece having a portion contained to fit over and to be releasably held by a patient's teeth and with means mounted to the mouthpiece for sensing at least one of the patient's vital signs of temperature, pulse and respiration. In a preferred embodiment, means are provided for sensing all three vital signs. The mouthpiece is formed from a pliable plastic-like material similar to that used in teeth guards used by athletes. The mouthpiece permits the patient to easily and accurately hold the various probes carried thereby at the proper location within the patient's mouth to insure optimum accuracy.

Another objective is to provide a probe comprising a mouthpiece having a portion with a notch for receipt of a patient'tongue frenulum when the mouthpiece is inserted into the patient's mouth and means mounted to the mouthpiece adjacent the notch and underlying the patient's tongue for sensing at least one of the patient's vital signs of temperature, pulse and respiration. Again, the notch in the mouthpiece permits the patient or the other person supervising use of the probe to accurately locate the sensors beneath the patient's tongue at the desired location and to easily hold those sensors at the desired locations for a sufficient time to make accurate measurement.

Yet a further object of the present invention is to provide a probe comprising a reflective photodetector for sensing both pulse and respiration of a patient, a mouthpiece insertable into a patient's mouth and means for mounting the reflective photodetector to the mouthpiece at a location where it will be adjacent to a part of the interior surface of the patient's mouth which relatively rapidly, periodically changes in reflectivity due to the patient's pulse and which relatively slowly, periodically changes in reflectivity due to the patient's respiration. As a result, the photodetector produces a single signal representative of both the patient's pulse and the patient's respiration. In one embodiment, the reflective photodetectors are mounted to a portion of the mouthpiece which underlies the patient's tongue, and in another embodiment, the photodetectors are pressed against the interior gum of the patient.

Still another object is to provide a probe with a mouthpiece having a portion adjacent a patient's gum when inserted in the patient's mouth and means carried by that portion for sensing the patient's temperature. It has been determined that accurate measurement can be made by pressing a thermistor against the interior gum of the patient and that location of the thermistor under the patient's tongue is not absolutely necessary. The present invention takes advantage of the fact by eliminating the portion of the probe which would otherwise have to be located beneath the patient's tongue which can be uncomfortable for the patient.

BRIEF DESCRIPTION OF THE DRAWINGS

The foregoing objects, features and advantages will be described in greater detail and further objects, features and advantages will be made apparent from a reading of the following detailed description of the preferred embodiment which is given with reference to the several views of the drawing, in which:

FIG. 1 is a top frontal perspective view of one embodiment of the probe of the present invention;

FIG. 2 is another perspective view of the probe of FIG. 1 as it would appear inserted in a patient's mouth;

FIG. 3 is a sectional view of the probe of FIG. 2 taken along section line III—III;

FIG. 4 is a lower, frontal perspective view of another embodiment of the probe of the present invention;

FIG. 5 is a upper, rearward perspective view of the probe of FIG. 4; and

FIG. 6 is a plan view of the probe of FIG. 4 illustrating its position as fitted over the lower teeth of a patient.

DETAILED DESCRIPTION

Referring to FIGS. 1-3, a first embodiment of the probe of the present invention is seen to comprise a mouthpiece 10 with an arcuate portion 12 which fits over the patient's lower teeth 14 and an inwardly extending, portion 16. Portion 16 is pie-shaped except in place of a peak, a V-shaped notch 18 has been provided. As best seen in FIG. 3, the inwardly extending portion 16 underlies the patient's tongue 20 with the tongue frenulum 22 received within the notch 18. Mounted to the interior portion 16 of mouthpiece 10 is a thermistor, thermocouple or other electronic temperature sensing device 24 and a photodetector 26. Preferably, photodetector 26 is a reflective photodetector having a light emitter 26a and a light receptor or detector 26b. Both sensing means, thermistor 24 and reflective photodetector 26 are located at the interior portion 16 of mouthpiece 10 and on opposite sides of slot 18 to isolate them from movement of the patient's tongue.

The reflectivity of the interior surface of the patient-'mouth, including the undersurface of the patient's tongue, will periodically fluctuate in accordance with the periodic fluctuation of the patient's pulse and the patient's respiration. The periodic changes in reflectivity due to the patient's respiration will of course be slower than the changes in reflectivity due to the faster pulse of the patient.

The reflective photodetector 26 operates on the same principle as a photoplethysmograph, and the photodetector 26 will produce a signal which carries both the pulse rate information and the respiration rate information. External circuitry 28 is provided for processing the information from the sensors 24 and 26 and displaying the temperature, pulse rate and respiration rate information derived therefrom. The external circuitry may also store the patient's identification or room number in association with the temperature pulse and respiration readings. The external circuitry 28 is coupled to the sensors through a suitable cable 30 which has a connector 32 connectable with a releasable mating connector 34 mounted to the mouthpiece 10 at the forward face 36 of the arcuate portion 12 which fits over the patient's teeth. The external circuitry 28 also provides the necessary electrical power to the sensors required by them to operate.

The cable 30 or the external circuitry 28 provides means for both A.C. coupling and D.C. coupling the output signal from the photodetector 26 to two different processing portions of the external circuitry 28. The A.C. coupled signal responds to changes in reflectivity caused by the pulsatile action of the arterial blood flow and thus is representative of pulse rate. This A.C. coupled signal is thus processed to produce a pulse rate indication. The D.C. coupled signal, on the other hand, fluctuates with the slower changes in reflectivity due to the expansion and contraction of the venal system which is in phase with the respiration of the patient. This D.C. signal is coupled to the processing portion of the circuit which produces an indication of the respiration rate of the patient.

The mouthpiece 12, itself, is formed from thermoformed plastic within which are mounted the sensors 24 and 26 and the leads interconnecting them with the releasable connector 34. In addition, the outer portion which fits over the patient's lower teeth and the other portions which come in contact with the patient's mouth are preferably formed from a suitable soft pliable material to protect the sensitive and delicate interior surface of the mouth from injury. Preferably, the mouthpiece 12 is similar to and as comfortable as the guards often worn by athletes. Disposable sheaths or covers can be fitted over the mouthpiece so that the same mouthpiece 12 may be repeatedly used from patient to patient without the need for sterilization after each use.

Referring now to FIGS. 4-6, another embodiment of the probe of the present invention will be described. As seen, this probe has a portion 12 which overlies the patient's lower teeth 14 and has a releasable connector 34 mounted to the front face 36 of portion 12, but is lacks the inwardly extending portion 16. Accordingly, the photosensor 26 and the thermistor 24 are mounted to portion 12 in a location adjacent the gum of the patient. Preferably, the sensors 24 and 26 are mounted to a portion of the mouthpiece which is pressed against the inner gum of the patient adjacent the third molar. The reflectivity changes of the gum of the patient adjacent the third molar correspond to like changes in the interior surface of the patient's mouth underlying the patient's tongue and the two probes function in an identical manner. Particularly advantageous in this second embodiment is that the thermistor 24 is found to accurately sense the temperature of the patient, even though it is not located underneath the patient's tongue. This of course eliminates the need to have a probe deeply inserted into the patient's mouth in a position underlying the patient's tongue which is often uncomfortable to the patient.

While two particular embodiments of the present invention have been disclosed in detail, it should be appreciated that numerous variations may be made without departing from the scope of the invention as claimed. For instance, the advantages of the inwardly extending probe portion 16 with the V-shaped slot 18 can be employed without the mouthpiece portion 12 overlying the lower front teeth. In addition, the protodetectors 26 can be located adjacent the patient's gum, as illustrated in FIGS. 4-6, with the thermistor still being located at the inwardly projecting portion 16 underlying the patient's tongue. Likewise, although the V-shaped slot 18 is advantageously employed to properly locate the sensors, the sensors could otherwise be properly located and would still function in accordance with the invention. It is contemplated that the sensors mounted adjacent the patient's gum could also be located adjacent other interior portions of the patient's mouth which fluctuate in reflectivity in the same or similar fashion, as described.

We claim:
1. A probe, comprising:
a mouthpiece having a portion contoured to fit over a substantial portion of at least some of a patient's teeth; and
means for electronically sensing the temperature of the patient's gum within the patient's mouth,
said temperature sensing means being mounted to said mouthpiece in sensing relationship with the interior of the patient's mouth,
said contoured portion, when fitted over the patient's teeth, holding the mouthpiece and thus the sensing means against any substantial movement relative to said teeth, and said contoured portion also being fitted over the patient's gum and said temperature sensing means being held against the patient's gum by said contoured portion to sense the temperature of the patient's gum.

2. The probe of claim 1 in which said arcuate member which overlaps the patient's gum adjacent the teeth and a contoured portion has an channel within which the patient's teeth are received, and said sensing means is mounted thereby against the patient's gum in sensing proximity.

3. A probe, comprising:
a mouthpiece having a portion contoured to fit over a substantial portion of at least some of a patient's teeth; and
means for electronically sensing the temperature within the patient's mouth,
said sensing means being mounted to said mouthpiece in sensing relationship with the interior of the patient's mouth, and
said contoured portion, when fitted over the patient's teeth, holding the mouthpiece and thus the sensing means against any substantial movement relative to said teeth,
said mouthpiece including a member mounted to said contoured portion and extending therefrom within the patient's mouth and beneath the underside of the patient's tongue, and said temperature sensing means being mounted to said member at a notch for receipt of the tongue frenulum, and
said temperature sensing means being mounted at said notch and in sensing relationship with the frenulum and the underside of the patient's tongue when the frenulum is received within said notch.

4. A probe, comprising:
a mouthpiece having a portion contoured to fit over a substantial portion of at least some of a patient's teeth; and
means for electronically sensing within the patient's mouth at least one of the patient's vital signs of temperature, pulse and respiration,
said sensing means being mounted to said mouthpiece in sensing relationship with the interior of the patient's mouth, and
said contoured portion, when fitted over the patient's teeth, holding the mouthpiece and thus the sensing means against any substantial movement relative to said teeth, and
said sensing means including means for sensing the patient's pulse.

5. The probe of claim 4 in which said pulse sensing means comprises a photodetector for sensing changes in reflectivity of the interior surface of the patient's mouth.

6. The probe of claim 5 in which said pulse sensing means is mounted to a member held by said portion at a location contiguous with the underside of the patient's tongue.

7. The probe of claim 6 in which said portion has a notch for receipt of the patient's tongue frenulum.

8. The probe of claim 4 in which said pulse sensing means is held by said portion against the patient's gum.

9. The probe of claim 4 in which said sensing means includes means for sensing the patient's respiration.

10. The probe of claim 9 in which both said pulse sensing means and said respiration sensing means share a common detector element.

11. The probe of claim 10 in which said common detector element comprises a photodetector.

12. The probe of claim 4 in which said sensing means includes means for sensing the patient's temperature.

13. A probe, comprising:
a mouthpiece having a portion contoured to fit over a substantial portion of at least some of a patient's teeth; and
means for electronically sensing within the patient's mouth at least one of the patient's vital signs of temperature, pulse and respiration,
said sensing means being mounted to said mouthpiece in sensing relationship with the interior of the patient's mouth, and
said contoured portion, when fitted over the patient's teeth, holding the mouthpiece and thus the sensing means against any substantial movement relative to said teeth,
said sensing means including means for sensing the patient's respiration.

14. The probe of claim 13 in which said respiration sensing means is held by said portion against the patient's gum.

15. The probe of claim 13 in which said respiration sensing means is mounted to said portion by means for holding the sensing means at the underside of the patient's tongue.

16. The probe of claim 15 in which said portion has a notch for receiving the patient's tongue frenulum.

17. The probe of claim 13 in which said respiration sensing means comprises a photodetector.

18. The probe of claim 17 in which said photodetector also senses the patient's pulse.

19. A probe, comprising:
a mouthpiece having a portion contoured to fit over a substantial portion of at least some of a patient's teeth; and
means for electronically sensing within the patient's mouth at least one of the patient's vital signs of temperature, pulse and respiration,
said sensing means being mounted to said mouthpiece in sensing relationship with the interior of the patient's mouth, and
said contoured portion, when fitted over the patient's teeth, holding the mouthpiece and thus the sensing means against any substantial movement relative to said teeth,
said mouthpiece including an arcuate member with a channel for receipt of a patient's teeth therewithin,
said mouthpiece including a second member connected with said arcuate member and underlying the patient's tongue, and said sensing means being mounted to said second member in a position underlying the patient's tongue.

20. A probe, comprising:
a mouthpiece having a portion contoured to fit over a substantial portion of at least some of a patient's teeth; and
means for electronically sensing within the patient's mouth at least one of the patient's vital signs of temperature, pulse and respiration,
said sensing means being mounted to said mouthpiece in sensing relationship with the interior of the patient's mouth, and said contoured portion, when fitted over the patient's teeth, holding the mouthpiece and thus the sensing means against any substantial movement relative to said teeth, said sensing means comprising a photodetector responsive to visual tone changes due to capillary action of blood vessels in the interior surface of the patient's mouth and said mouthpiece holding said photodetector against the interior surface when inserted over the patient's teeth.

21. The probe of claim 4, 13, 19 or 20 in which said sensing means includes means for sensing the patient's temperature.

22. The probe of claims 3, 5, 6, 14, 19 or 20 in which said mouthpiece is contoured to fit over the patient's lower teeth.

23. The probe of claims 3, 5, 6, 13, 19 or 20 in which said contoured portion of the mouthpiece comprises an arcuate member with a channel for receipt of a patient's teeth therewithin.

24. The probe of claims 1, 3, 4, 13, 19 or 20 in which said mouthpiece is made of a soft plastic-like material to protect the patient's mouth from injury.

25. A probe, comprising:
a mouthpiece having a member with a notch for receipt of a patient's tongue frenulum when the mouthpiece is inserted into the patient's mouth; and
means mounted to the member at the notch for electronically sensing at least one of the patient's vital signs of temperature, pulse and respiration.

26. The probe of claim 25 in which said sensing means includes means for sensing the patient's temperature.

27. The probe of claim 26 in which said temperature patient's temperature.

28. The probe of claim 26 in which said sensing means includes means for sensing the patient's pulse, and in which the pulse sensing means is mounted at one side of the notch and the temperature sensing means is mounted at the other side of the notch.

29. The probe of claim 28 in which said pulse sensing means comprises a photodetector for sensing periodic changes in the reflectivity of the interior surface of the patient's mouth caused by the patient's pulse.

30. The probe of claim 26 in which said sensing means includes means for sensing the patient's respiration and in which the respiration sensing means is mounted at one side of the notch and the temperature sensing means is mounted at the other side of the notch.

31. The probe of claim 30 in which said respiration sensing means comprises a photodetector for sensing periodic changes in reflectivity of the interior surface of the patient's mouth caused by the patient's respiration.

32. The probe of claim 25 or 28 in which said sensing means includes means for sensing the patient's pulse.

33. The probe of claim 32 in which said pulse sensing means comprises a photodetector.

34. The probe of claim 32 in which said sensing means includes means for sensing the patient's respiration.

35. The probe of claim 25 in which said sensing means includes means having a sensing element for sensing both pulse and respiration.

36. The probe of claim 35 in which said sensing means includes means for sensing temperature, and in which said temperature sensing means is mounted on one side of the notch and said sensing element is mounted on the other side of the notch.

37. A probe, comprising:
a reflective photodetector for sensing both pulse and respiration of a patient;
a mouthpiece insertable into a patient's mouth;
means for mounting the reflective photodetector to the mouthpiece at a location where it will be in adjacent sensing relationship with a part of the interior surface of the patient's mouth which relatively rapidly, periodically changes in reflectivity due to the patient's pulse and which relatively slowly, periodically changes in reflectivity due to the patient's respiration, said photodetector producing a single signal representative of both the relatively rapid and the relatively slower changes in reflectivity.

38. The probe of claim 37 in which said photodetector is mounted to the mouthpiece at a location within the patient's mouth and in sensing relationship with the gum adjacent the patient's third molar.

39. The probe of claim 37 in which said photodetector is mounted to the mouthpiece adjacent the inner side of the patient's gum and within the patient's mouth.

40. The probe of claim 37 in which said photodetector is mounted to the mouthpiece in adjacent sensing relationship with the tongue frenulum of the patient when inserted within the patient's mouth.

41. The probe of claim 40 including
means for sensing the patient's temperature, and
means for mounting said temperature sensing means to the mouthpiece in adjacent sensing relationship with the other side of the patient's tongue frenulum when inserted within the patient's mouth.

42. The probe of claim 41 in which said mouthpiece has a notch for receipt of the patient's tongue frenulum, said photodetector being mounted to the mouthpiece at one side of the notch and said temperature sensing means being mounted to the other side of the notch.

43. The probe of claim 37 in which said probe includes means for sensing the patient's temperature and means for mounting said temperature sensing means to the mouthpiece at a location adjacent the patient's gum.

44. The probe of claim 3 in which said photodetector is mounted to said mouthpiece at the underside of the patient's tongue and within the patient's mouth.

45. The probe of claim 37 in which
said mouthpiece has a generally U-shaped portion within which the patient's teeth are received, and
said photodetector is mounted to said generally U-shaped portion.

46. The probe of claim 37 in which a portion of the signal representative of the patient's pulse is filterable from said portion of the signal representative of the patient's respiration by means of A.C. coupling.

47. A probe, comprising:
a mouthpiece having a portion adjacent a patient's gum when inserted in the patient's mouth;
means carried by said portion for sensing the patient's temperature, and
other means for sensing the patient's respiration and means for mounting the respiration sensing means to the mouthpiece, said other sensing means being mounted to another portion adjacent the patient's gum.

48. A probe, comprising:
a mouthpiece having a portion adjacent a patient's gum when inserted in the patient's mouth; and
means carried by said portion for sensing the patient's temperature; and
other means for sensing the patient's respiration and means for mounting the respiration sensing means to the mouthpiece, said other sensing means being mounted to a portion of the mouthpiece underlying the patient's tongue.

* * * * *

UNITED STATES PATENT AND TRADEMARK OFFICE
CERTIFICATE OF CORRECTION

PATENT NO. : 4,510,941
DATED : Apr. 16, 1985
INVENTOR(S) : Carolyn M. Semrow, Mark W. Kolstedt and William J. Dunn It is certified that error appears in the above-identified patent and that said Letters Patent is hereby corrected as shown below:

Col. 3, lines 23 and 24, change "patient-'mouth," to - patient's mouth, -;

Col. 4, line 15, change "is" to - it -;

Col. 4, line 41, change "pro-" to - pho -;

Col. 5, line 6, after "said" insert - contoured portion has an -;

Col. 5, line 8, after "a" delete "contoured portion has an";

Col. 7, line 14, change "3, 5, 6, 14," to - 1, 3, 4, 13, -;

Col. 7, line 17, change "3, 5, 6," to - 1, 3, 4, -;

Col. 7, line 33, before "patient's" insert - sensing means includes a thermistor for sensing the -;

Col. 7, line 51, change "28" to - 26 -; and

Col. 8, line 37, change "3" to - 37 -.

Signed and Sealed this

Fifth Day of January, 1988

Attest:

DONALD J. QUIGG

*Attesting Officer*  *Commissioner of Patents and Trademarks*